US006969514B2

(12) United States Patent
Soll

(10) Patent No.: US 6,969,514 B2
(45) Date of Patent: Nov. 29, 2005

(54) METHOD FOR TREATING ELEVATED INTRAOCULAR PRESSURE, INCLUDING GLAUCOMA

(76) Inventor: David B. Soll, 7006 Dorsam Way, Ambler, PA (US) 19002

(*) Notice: Subject to any disclaimer, the term of this patent is extended or adjusted under 35 U.S.C. 154(b) by 0 days.

(21) Appl. No.: 10/358,466

(22) Filed: Feb. 5, 2003

(65) Prior Publication Data

US 2004/0151714 A1 Aug. 5, 2004

(51) Int. Cl.$^7$ ............... A61K 38/47; A61K 9/127
(52) U.S. Cl. ............... 424/94.62; 424/94.61; 424/428; 424/450
(58) Field of Search ............ 424/94.62, 94.61, 424/428, 450

(56) References Cited

U.S. PATENT DOCUMENTS

| | | | |
|---|---|---|---|
| 4,820,516 A | * 4/1989 | Sawyer et al. | 424/94.62 |
| 5,626,865 A | * 5/1997 | Harris et al. | 424/427 |
| 5,792,103 A | 8/1998 | Schwartz et al. | |
| 6,039,943 A | 3/2000 | Karageozian et al. | |
| 6,306,993 B1 | 10/2001 | Rothbard et al. | |
| 6,495,663 B1 | 12/2002 | Rothbard et al. | |
| 6,537,545 B1 | * 3/2003 | Karageozian et al. | 424/94.4 |
| 6,593,292 B1 | 7/2003 | Rothbard et al. | |
| 6,605,115 B1 | 8/2003 | Cooke et al. | |
| 6,610,292 B2 | * 8/2003 | Karageozian et al. | 424/94.62 |
| 6,669,951 B2 | 12/2003 | Rothbard et al. | |
| 6,730,293 B1 | 5/2004 | Rothbard et al. | |
| 6,745,776 B2 | * 6/2004 | Soll | 128/898 |
| 6,759,387 B2 | 7/2004 | Rothbard et al. | |
| 2002/0009491 A1 | 1/2002 | Rothbard et al. | |
| 2002/0131965 A1 | 9/2002 | Rothbard et al. | |
| 2003/0022831 A1 | 1/2003 | Rothbard et al. | |
| 2003/0032593 A1 | 2/2003 | Wender et al. | |
| 2003/0083256 A1 | 5/2003 | Rothbard et al. | |
| 2003/0162719 A1 | 8/2003 | Rothbard et al. | |
| 2003/0175849 A1 | * 9/2003 | Schwartz et al. | 435/29 |
| 2003/0185788 A1 | 10/2003 | Rothbard et al. | |
| 2004/0074504 A1 | 4/2004 | Cooke et al. | |
| 2004/0161405 A9 | 8/2004 | Rothbard et al. | |
| 2004/0186045 A1 | 9/2004 | Rothbard et al. | |

FOREIGN PATENT DOCUMENTS

| | | |
|---|---|---|
| EP | 0 975 370 B1 | 10/2003 |
| WO | WO 01/62297 A1 | 8/2001 |
| WO | WO 00/74701 A2 | 3/2002 |
| WO | WO 00/74701 A3 | 3/2002 |
| WO | WO 02/065986 A2 | 8/2002 |
| WO | WO 02/065986 A3 | 8/2002 |
| WO | WO 02/069930 A1 | 9/2002 |
| WO | WO 2003/049772 A2 | 6/2003 |
| WO | WO 2003/049772 A3 | 6/2003 |
| WO | WO 2004/016220 A2 | 2/2004 |

OTHER PUBLICATIONS

American Academy of Ophthalmology, "Adverse Effects Associated with the Absence of Hyaluronidase in Anesthesia for Cataract Surgery", www.aao.org/aao/education/library/rcr_hyaluronidase.cfm. (Feb. 2001).
Budavari, Susan, Ed., et al., "Hyaluronic Acid", Monograph 4675 in the Merck Index, 11 Ed.. Merck & Co., In., (Rahway, NJ), pp. 751-752, (1989).
Calder, I.G., et al., "Hyaluronidase and Sodium Hyaluronate in Cataract Surgery", *British Journal of Ophthalmology*, 70, 418-420, (1986).
Equi, Robert A., et al., "Hyaluronan Polymer Size Modulates Intraocular Pressure", *Journal of Ocular Pharmacology and Therapeutics*, 13(4). 289-295. (1997).
Fechner, Paul U., et al., "Intraocular Use of Hyaluronidase to Dissolve Sodium Hyaluronic Acid", *Journal of Refractive Surgery*, 13. 502-503. (Sep./Oct. 1997).
Hein, Stephen R., et al., "Elimination of Sodium Hyaluronate-Induced Decrease in Outflow Facility With Hyaluronidase", *Ophthalmic Surgery*. 17(11). 731-734. (Nov. 1986).
Physician's Desk Reference in Ophthalmology, pp. 11-21, (2000).
Rankova, Charita B., "Application of Hyaluronidase After Unsuccessful Trabeculectomy", *Documenta Ophthalmologica*, 80. 381-383. (1992).
Rouhi, Maureen A., "Simple Molecules Aid Drug Uptake", *Chemical and Engineering News*. pp. 49-50. (Jan. 2001).

* cited by examiner

*Primary Examiner*—Herbert J. Lilling
(74) *Attorney, Agent, or Firm*—Akin Gump Strauss Hauer & Feld, LLP

(57) ABSTRACT

Hyaluronic acid, a polymer found in the trabecular meshwork of the eye, has a polymeric structure that is broken down by the enzyme hyaluronidase. A method is provided for reducing elevated intraocular pressure in an eye of a patient, such as a patient suffering from glaucoma, by administering modified hyaluronidase to the surface of the eye as a drop, spray, ointment, sustained-release or non-sustained release unit, and allowing the hyaluronidase to remain within the anterior chamber of the eye. The hyaluronidase is modified to enhance penetration through the corneal barrier, and is administered in an amount effective to reduce an elevated intraocular pressure. The method thus reduces the elevated intraocular pressure in the eye of a glaucoma patient without undesirable side effects.

14 Claims, No Drawings

METHOD FOR TREATING ELEVATED INTRAOCULAR PRESSURE, INCLUDING GLAUCOMA

BACKGROUND OF THE INVENTION

Glaucoma is a disease of the eye in which intraocular pressure rises to abnormal levels. In the human eye, a fluid called the aqueous humor functions to maintain the pressure in the eye at a level slightly above atmospheric pressure: a normal intraocular pressure is about 15 mm Hg gauge. The aqueous humor keeps the globe of the eye firm and provides nutrition for the lens and the cornea. The aqueous humor is constantly secreted by the ciliary body and is drained away at the base of the iris via a series of channels known as the trabecular meshwork. When these outflow channels become blocked, the pressure in the eye increases and the circulation of blood to the optic nerve and other parts of the eye is restricted. Such a condition is known as glaucoma. If the intraocular pressure remains elevated for prolonged time periods, the fibers of the optic nerve may atrophy and the retina may lose function.

Current methods for relieving intraocular pressure increases in the eye include various types of eyedrops such as beta-adrenergic blocking agents, sympathomimetic agents, miotics, alpha II selective agents, carbonic anhydrase inhibitors and prostaglandin agents. Tables of some of these agents appear in the *Physician's Desk Reference in Ophthalmology* 2000, pages 11–12. These medications work to lower the intraocular pressure by either reducing aqueous humor formation or by increasing the amount of aqueous humor outflow (removal) from the anterior chamber of the eye.

Such methods for relieving the intraocular pressure are often undesirable due to the side effects of many of these drugs. For example, carbonic anhydrase inhibitors may cause lethargy and, in some instances, disorientation. Beta-blocker medications may be contraindicated in patients with breathing problems or slow heart rates. An increase in blood pressure may result from sympathomimetic drugs. Finally, parasympathomimetic drugs may be associated with retinal detachments in eyes with peripheral retinal and retinovascular diseases.

Therefore, there remains a need in the art for a method of relieving intraocular pressure in glaucoma patients without afflicting the patient with a variety of undesirable side effects.

BRIEF SUMMARY OF THE INVENTION

According to the present invention, a method for reducing elevated intraocular pressure in an eye comprises administering to the eye modified hyaluronidase in an amount effective to reduce the intraocular pressure to a normal level.

DETAILED DESCRIPTION OF THE INVENTION

Hyaluronic acid is a natural, high molecular weight, highly viscous polymer consisting of alternating acetylglycosamine and glucuronic acid units. This acid is found in the trabecular meshwork as well as in the vitreous humor of the eye, as well as in other locations in the body. Hyaluronidase is an enzyme that cleaves glycosidic bonds, thereby breaking down the polymeric structure of hyaluronic acid. One highly preferred form of hyaluronidase is the Wyadase™ preparation, formerly commercially available from Wyeth-Ayerst. However, alternative preparations of hyaluronidase may be used if they are highly purified. Any type of pure non-antigenic preparation of hyaluronidase may be used in this invention as well.

This invention is particularly directed to a method for using hyaluronidase in the treatment of patients with chronic open angle glaucoma and other forms of glaucoma in which outflow of the aqueous humor is prevented because of poor function of the trabecular meshwork. The method involves reducing intraocular pressure in an eye of a glaucoma patient by administering to the eye a modified form of hyaluronidase. The term "modified hyaluronidase" refers to a molecule that has been modified either by formulation or structural modification. For example, modified forms include, but are not limited to, a liposome formulation of hyaluronidase and transporters of oligomers of arginine or arginine-like monomers which are linked to the hyaluronidase molecule. Such forms may include di-, tri-, or tetra-arginine derivatives prepared in an acceptable ophthalmic formulation in such a way as to enhance penetration through the corneal barrier. Modified hyaluronidase may also be provided in the form of cochleates. These modifications thus allow the hyaluronidase to enter the anterior chamber of the eye in an active form, namely, a form which can break down hyaluronic acid.

In a preferred embodiment, the modified hyaluronidase may be administered in liposomes as eyedrops and thus pass into the anterior chamber through the corneal barrier. The concentration of hyaluronidase in the eyedrops and the frequency of administration are in amounts effective to lower an individual's intraocular pressure to within as normal a limit as possible. For a typical patient, a normal level is less than about 20 mm Hg gauge, and usually about 10 to about 18 mm Hg. However, this must be individualized for a given patient. Once in the anterior chamber of the eye, the concentration of the active hyaluronidase is about 2 to 25 USP units per ml aqueous humor, more preferably about 2 to 10 USP units.

Although it is preferred that the modified hyaluronidase be administered topically to the eye in liposomes as eyedrops, it may be administered to the eye by any method known in the art, Such as, but not limited to, gelable drops, spray, ointment, or a sustained or non-sustained release unit placed in a conjunctival cul-de-sac of the eye. Any type of transport mechanism can be attached to the hyaluronidase, or the hyaluronidase may be packaged in such a mechanism, to allow it to pass though the cornea. The modified hyaluronidase drop is preferably administered to the surface of the eye and is thereby absorbed through the cornea into an anterior chamber of the eye in an active form. In a preferred embodiment, the hyaluronidase is left in the eye following administration.

By treating an eye of a glaucoma patient with modified hyaluronidase, the intraocular pressure may be reduced. Such a method may be effective at relieving the intraocular pressure because the trabecular meshwork of the eye contains hyaluronic acid. As described above, the hyaluronidase serves to break down the hyaluronic acid by cleaving the glycosidic bonds, thereby relieving the pressure by breaking down some of the hyaluronic acid in the trabecular meshwork, which is the main drainage area for the aqueous humor fluid in the eye. This partial breakdown will enhance the outflow of aqueous humor and thus lower the intraocular pressure. If a series of administrations of such modified hyaluronidase drops is administered to an eye, the intraocular pressures may be lowered for a prolonged period of time.

Traditionally, if a patient's intraocular pressure were significantly elevated, it would have been necessary to administer large doses of carbonic anhydrase inhibitors or topical eyedrops, such as beta-blockers or Alpha II agonists, in order to decrease aqueous formation and/or increase aqueous outflow. These agents all have significant side effects and, in some instances, are contraindicated in patients with various types of medical conditions, such as breathing problems, heart disease or high blood pressure. However, the use of modified hyaluronidase in these situations will eliminate the necessity of giving such patients large doses of these drugs.

Consequently, the topical use of modified hyaluronidase in the form of drops, gels, ointments or sprays, for example, has many advantages over traditional medications used to treat glaucoma, and is thus attractive as a new form of treatment that does not have known side effects. Such a modified hyaluronidase treatment thus fulfills a long-felt need in the art for a glaucoma treatment which is effective, does not cause significant undesirable side effects, and which is appropriate even in patients with existing medical conditions.

It has previously been shown that injection of hyaluronidase prevented pressure rises when hyaluronic acid was instilled in the anterior chamber of rabbit eyes; thereby demonstrating that the hyaluronidase was effective at breaking down the hyaluronic acid in the eye. Further, addition of the hyaluronidase to the eye caused no negative side effects. Such results are promising for treating glaucoma patients.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A method for reducing elevated intraocular pressure in an eye comprising topically administering to the eye of a patient modified hyaluronidase, wherein the hyaluronidase is structurally modified with a transporter and is administered in an amount effective to reduce the intraocular pressure to a normal level, wherein the modified hyaluronidase is absorbed through a cornea into an anterior chamber of the eye.

2. The method according to claim 1, wherein the elevated intraocular pressure is caused by glaucoma.

3. The method according to claim 1, wherein the effective amount of modified hyaluronidase administered to the eye is about 5 to 25 USP units per ml.

4. The method according to claim 1, further comprising leaving the hyaluronidase in the eye following administration.

5. The method according to claim 1, wherein the modified hyaluronidase is administered to the eye as a drop, a spray, or an ointment.

6. The method according to claim 1, wherein the modified hyaluronidase is administered to the eye by a sustained or non-sustained release unit placed in a conjunctival cul-de-sac of the eye.

7. The method according to claim 1, wherein the effective amount of modified hyaluronidase administered to the eye is sufficient to achieve a hyaluronidase concentration of about 2 to about 25 USP units per ml aqueous humor in the anterior chamber of the eye.

8. The method according to claim 1, wherein the modified hyaluronidase is part of a liposome preparation.

9. The method according to claim 1, wherein the modified hyaluronidase is in the form of a gelable drop.

10. The method according to claim 1, wherein the hyaluronidase is modified with a transporter of oligomers of arginine or arginine-like monomers linked to a hyaluronidase molecule.

11. The method according to claim 1, wherein the normal level of intraocular pressure is less than about 20 mm Hg gauge.

12. The method according to claim 11, wherein the normal level of intraocular pressure is about 10 to about 18 mm Hg gauge.

13. The method according to claim 1, wherein the modified hyaluronidase is administered to the eye repeatedly and wherein the intraocular pressure remains at a normal level.

14. A method for reducing elevated intraocular pressure in an eye comprising topically administering to the eve of a patient modified hyaluronidase, wherein the modified hyaluronidase is in a form of a cochleate and is administered in an amount effective to reduce the intraocular pressure to a normal level.

* * * * *